(12) United States Patent
Sirkett

(10) Patent No.: US 11,413,762 B2
(45) Date of Patent: Aug. 16, 2022

(54) METHOD AND DEVICE FOR IDENTIFYING OBJECTS

(71) Applicant: ABB Schweiz AG, Baden (CH)

(72) Inventor: Daniel Sirkett, Fjärdhundra (SE)

(73) Assignee: ABB Schweiz AG, Baden (CH)

( * ) Notice: Subject to any disclaimer, the term of this patent is extended or adjusted under 35 U.S.C. 154(b) by 295 days.

(21) Appl. No.: 16/489,942

(22) PCT Filed: Mar. 10, 2017

(86) PCT No.: PCT/EP2017/055694
§ 371 (c)(1),
(2) Date: Aug. 29, 2019

(87) PCT Pub. No.: WO2018/162080
PCT Pub. Date: Sep. 13, 2018

(65) Prior Publication Data
US 2019/0389070 A1 Dec. 26, 2019

(51) Int. Cl.
*B25J 9/16* (2006.01)
*A61B 50/33* (2016.01)
*G06V 20/10* (2022.01)

(52) U.S. Cl.
CPC .............. *B25J 9/1697* (2013.01); *A61B 50/33* (2016.02); *B25J 9/1679* (2013.01); *G06V 20/10* (2022.01);
(Continued)

(58) Field of Classification Search
CPC ...... B25J 9/1697; B25J 9/1679; B25J 9/0087; B25J 15/0253; B25J 19/023; G06K 9/00664; A61B 50/33; G06V 20/10; G05B 2219/31045; G05B 2219/40053; G05B 2219/40564; G05B 2219/45047;
(Continued)

(56) References Cited

U.S. PATENT DOCUMENTS 7,997,847 B2 * 8/2011 Treat ...................... G16H 40/40
414/222.01
9,168,104 B2 * 10/2015 Dein ....................... A61B 90/96
(Continued)

FOREIGN PATENT DOCUMENTS

EP 2578366 A2 4/2013
WO WO-8901850 A1 * 3/1989 ............ B25J 9/1669

OTHER PUBLICATIONS

European Office Action; Application No. 17711 110.1; dated Mar. 2, 2021; 10 Pages.
(Continued)

*Primary Examiner* — Abby Y Lin
*Assistant Examiner* — Dylan Brandon Mooney
(74) *Attorney, Agent, or Firm* — Whitmyer IP Group LLC

(57) ABSTRACT

A method performed by a robotic system, for identifying single objects from a random assortment of objects. The robotic system picks, among a random assortment of objects on a presentation surface, an object from the presentation surface at a determined picking point. The robotic system removes any remaining objects from the presentation surface. The robotic system places the picked object on the presentation surface. The robotic system further analyzes the picked object on the presentation surface, in order to identify a single object.

19 Claims, 9 Drawing Sheets

(52) U.S. Cl.
CPC .............. *G05B 2219/31045* (2013.01); *G05B 2219/40053* (2013.01); *G05B 2219/40564* (2013.01); *G05B 2219/45047* (2013.01); *G05B 2219/45063* (2013.01); *Y02P 90/02* (2015.11)

(58) Field of Classification Search
CPC ........... G05B 2219/45063; G05B 2219/40537; Y02P 90/02
See application file for complete search history.

(56) References Cited

U.S. PATENT DOCUMENTS

| | | |
|---|---|---|
| 2010/0004778 A1 | 1/2010 | Arimatsu et al. |
| 2013/0006423 A1 | 1/2013 | Ito et al. |
| 2014/0147240 A1* | 5/2014 | Noda ..................... B25J 19/021 414/751.1 |
| 2015/0224650 A1* | 8/2015 | Xu ......................... B25J 9/1697 700/213 |

OTHER PUBLICATIONS

Interational Preliminary Report of Patentability Application No. PCT/EP2017/055694 dated Sep. 10, 2019 12 pages.

International Search Report and Written Opinion of the International Searching Authority Application No. PCT/EP2017/055694 Completed: Nov. 22, 2017; dated Nov. 30, 2017 15 pages.

\* cited by examiner

METHOD AND DEVICE FOR IDENTIFYING OBJECTS

TECHNICAL FIELD

The embodiments herein relate to a method and a device for identifying objects such as e.g. surgical instruments.

BACKGROUND

In facilities, such as in hospitals, laboratories and/or other health care facilities, different sets of objects are used for different procedures. After being used in a procedure, the objects are cleaned and sterilized in order to prepare the objects for re-use. In hospitals for example, instrument trays are pre-prepared kits containing a specific set of instruments required for a particular surgery. Following their use in a surgical procedure, the instruments are returned to their tray before leaving an operating theatre. The instruments are sent to a sterile processing facility, where the trays are passed through disinfecting machines akin to industrial dish-washing machines. Upon emerging from the disinfecting machines, the contents of the trays are removed at inspection stations. The instruments, which are often similar in appearance and made from highly reflective stainless steel, lie in an unordered jumble and may be tangled up in each other. In order to prepare a new tray of instruments for an upcoming surgical procedure, single instruments have to be identified and extracted from the unordered jumble of instruments. Identifying individual instruments, determining their location in the tray and directing grasping of an individual instrument can thus be a very complicated process, which usually requires a high amount of manual interaction.

SUMMARY

An object of the embodiments disclosed herein is therefore to provide an improved method for identifying objects, such as instruments.

According to a first aspect of embodiments herein the object is achieved by a method performed by a robotic system, for identifying single objects from a random assortment of objects. The robotic system picks, among a random assortment of objects on a presentation surface, an object from the presentation surface at a determined picking point. The robotic system transfers any remaining objects on the presentation surface to a compartment arranged below the presentation surface by moving the presentation surface from a first position to a second position. The robotic system places the picked object on the presentation surface. The robotic system further analyzes the picked object on the presentation surface, in order to identify a single object.

By picking an object at the determined picking point and removing the remaining objects from the presentation surface, the number of objects that have to be taken into consideration when identifying a single object can be reduced. Thereby a probability of a successful identification is increased.

In some embodiments, the remaining objects may be removed from the presentation surface by transferring the remaining objects from the presentation surface to a compartment arranged below the presentation surface. This may be performed by moving the presentation surface from a first position to a second position.

In some embodiments, the robotic system may place a random assortment of objects on the presentation surface. By making a first random selection from the plurality of objects delivered to the robotic system, a rough first limitation of the assortment of objects to be analyzed may be achieved.

In some embodiments the robotic system may further analyze the random assortment of objects placed on the presentation surface in order to identify a single object out of the random assortment.

In some embodiments, the robotic system may further determine a precision picking point, when the single object has been successfully identified. The precision picking point allows the picking tool to be directed, e.g. by the robotic system, to a specific location of the object, by which processing of the specific object is facilitated.

In some further embodiments, the robotic system may precision pick, such as pick in an accurate manner, the object at the determined precision picking point. Thereby, the processing, which may comprise closing and/or locking of jointed objects and/or the like, may be performed, while moving the object from the presentation surface to e.g. a second compartment.

The analyzing may comprise comparing an image of the objects on the presentation surface with stored images of the objects.

In some embodiments herein, the robotic system may further determine a picking point for the random assortment of objects arranged on the presentation surface, when the random assortment of objects has been analyzed and no single object is identified.

In some embodiments herein, the picking point is located furthest away, or almost furthest away, from a centroid of a bounding box of the objects on the presentation surface. By selecting the point furthest away from the centroid of the bounding box, a probability of only picking one single object is increased.

In some embodiments herein, the robotic system may further process the single object, when a single object is identified.

The processing may further comprise inspecting, lubricating and/or sharpness testing the object. The processing may further comprise positioning the object in a further compartment.

According to a second aspect of embodiments herein the object is achieved by a robotic system for identifying single objects from a random assortment of objects. The robotic system comprises a first robot arm which comprises a picking tool for picking objects. The robotic system comprises a separating apparatus comprising a frame having a first and a second section, a compartment arranged at the first section for housing objects, and a presentation surface movably arranged in the frame. The presentation surface is, in a first position, located in the first section of the frame and covers the compartment. In a second position the presentation surface is located in the second section and provides access to the compartment. The robotic system further comprises an analyzing apparatus for identifying objects, which objects are located on the presentation surface.

The moving presentation surface and the analyzing apparatus allow the robotic system to convert a 3D bin picking problem into a manageable 2D vision problem which facilitates the identification of the objects. It further provides an easy solution for reducing the assortment of objects to be analyzed, when no single object can be identified out of the random assortment of objects.

The frame of the separating apparatus may comprise a divider separating the first section from the second section. The divider may be arranged such that the divider prevents objects located on the presentation surface from entering the second section when the presentation surface moves from the first to the second section. Thereby an easy way of reducing the number of objects located on the presentation surface is provided, which facilitates the identification of a single object.

In some embodiments herein, the robotic system may comprise a second robot arm for moving the presentation surface between the first and the second sections. The presentation surface is movable between a first position, in which first position the presentation surface is substantially within the first section, and a second position, in which second position the presentation surface is substantially within the second section.

The analyzing apparatus may comprise an imaging device for generating an image of objects located on the presentation surface. The imaging device provides an easy way of identifying the object on the presentation surface by comparing an image of the object with images of objects to be identified stored in an imaging databank.

In some embodiments, the robotic system may comprise a further compartment for housing objects arranged at the second section. The presentation surface may provide access to the further compartment when the presentation surface is in the first position and cover the further compartment when the presentation surface is in the second position.

The embodiments herein thus provide an improved method and a system for identifying one object at a time from a random assortment of objects. Since the method and the system are able to reduce the selection of objects to be analyzed, a higher accuracy of identification can be achieved while at the same time reducing the amount of manual interaction required. Hence, the embodiments herein provide an efficient and accurate sorting system, e.g. compared to manual sorting.

DETAILED DESCRIPTION

Figure 1:
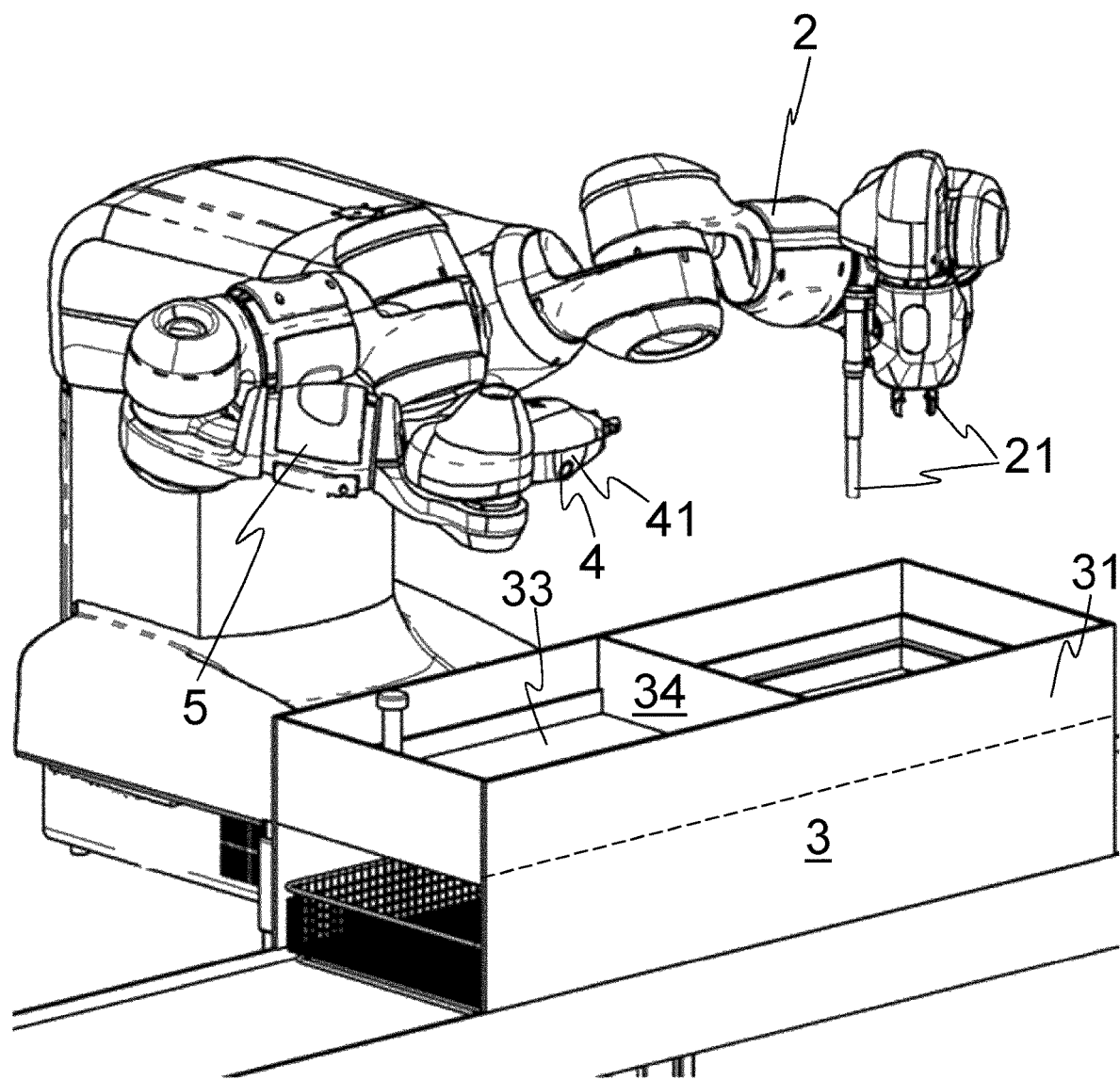
FIG. 1 illustrates the robotic system according to an embodiment herein.

FIG. 1 discloses an overview of a robotic system 1 for identifying single objects from a random assortment of objects 6 according to one embodiment herein. The robotic system 1 comprises a first robot arm 2 comprising at least one picking tool 21 for picking objects 6, a separating apparatus 3 and an analyzing apparatus 4 for identifying objects 6. The separating apparatus 3 comprises a presentation surface 33 being movably arranged between a first and a second position in a frame 31. In the first position the presentation surface 33 limits access to a compartment for housing objects and in the second position the presentation surface 33 provides access to the compartment for housing objects. The compartment may e.g. be located below the presentation surface. The presentation surface 33 may e.g. be tilted or be slidably arranged in the frame 31. In the embodiment shown in FIG. 1 the presentation surface 33 can be slidably moved between two sections of the separating apparatus 3, the sections being separated by a divider 34. The picking tool 21 may e.g. be a universal gripper, such as a telescopic magnetic gripper or a claw-type gripper. In some embodiments the first robot arm 2 may further comprise a main servo gripper.

The analyzing apparatus 4 for identifying objects 6, located on the presentation surface 33, may comprise an imaging device 41 for generating an image of the objects 6 located on the presentation surface 33. The imaging device 41 may e.g. comprise a camera and imaging software for generating and comparing a 2D image of the objects 6 with images of objects 6 stored in an imaging databank. The analyzing apparatus 4 may further comprise a storage, such as a memory, for storing an image databank of objects 6 to be identified. The analyzing apparatus 4 may be configured to compare the image generated by the imaging device 41 with images of objects 6 stored in the imaging databank.

In some embodiments, the analyzing apparatus 4 may instead of or in combination with the imaging device 41 also comprise an RFID tag reader, such as a pickup coil embedded in the presentation surface 33, for identifying objects 6 located on the presentation surface 33. The objects 6 are equipped with RFID tags in these embodiments.

In some embodiments, as shown in FIG. 1, the robotic system 1 may comprise a second robot arm 5. The second robot arm 5 may be configured to move the presentation surface 33 between the first and the second sections or to house the analyzing apparatus 4.

Figure 2A:
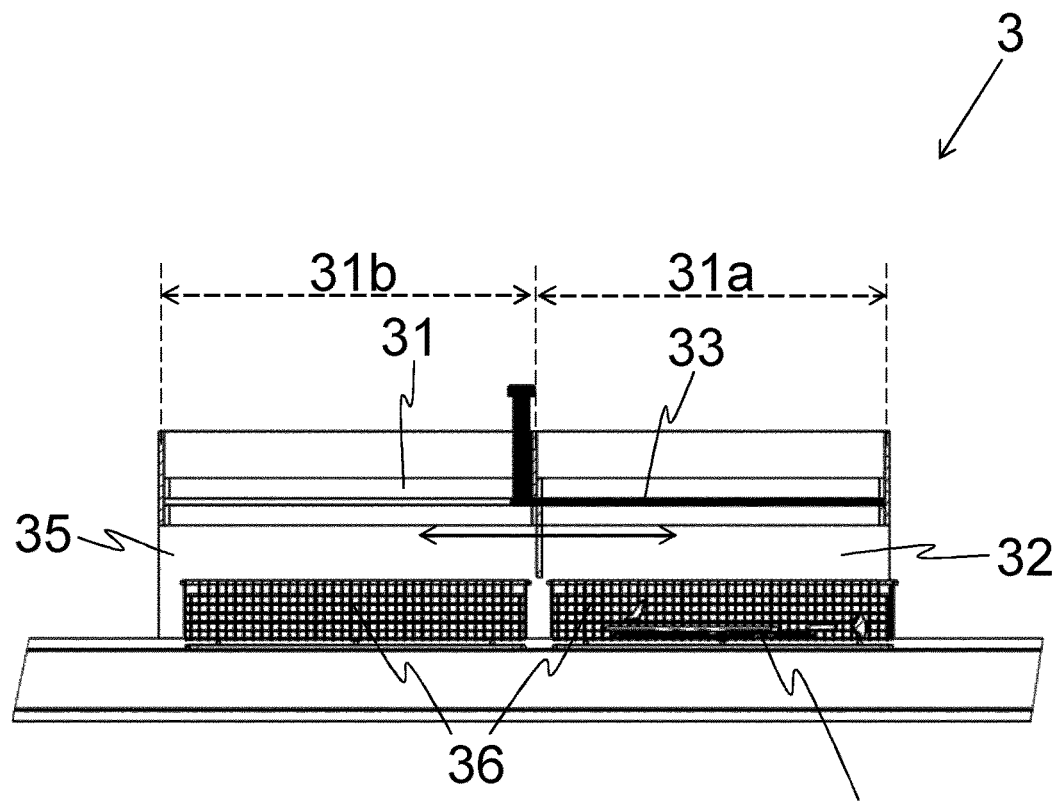
FIG. 2a illustrates an example of the separating apparatus herein, with the presentation surface in a first position.
Figure 2B:
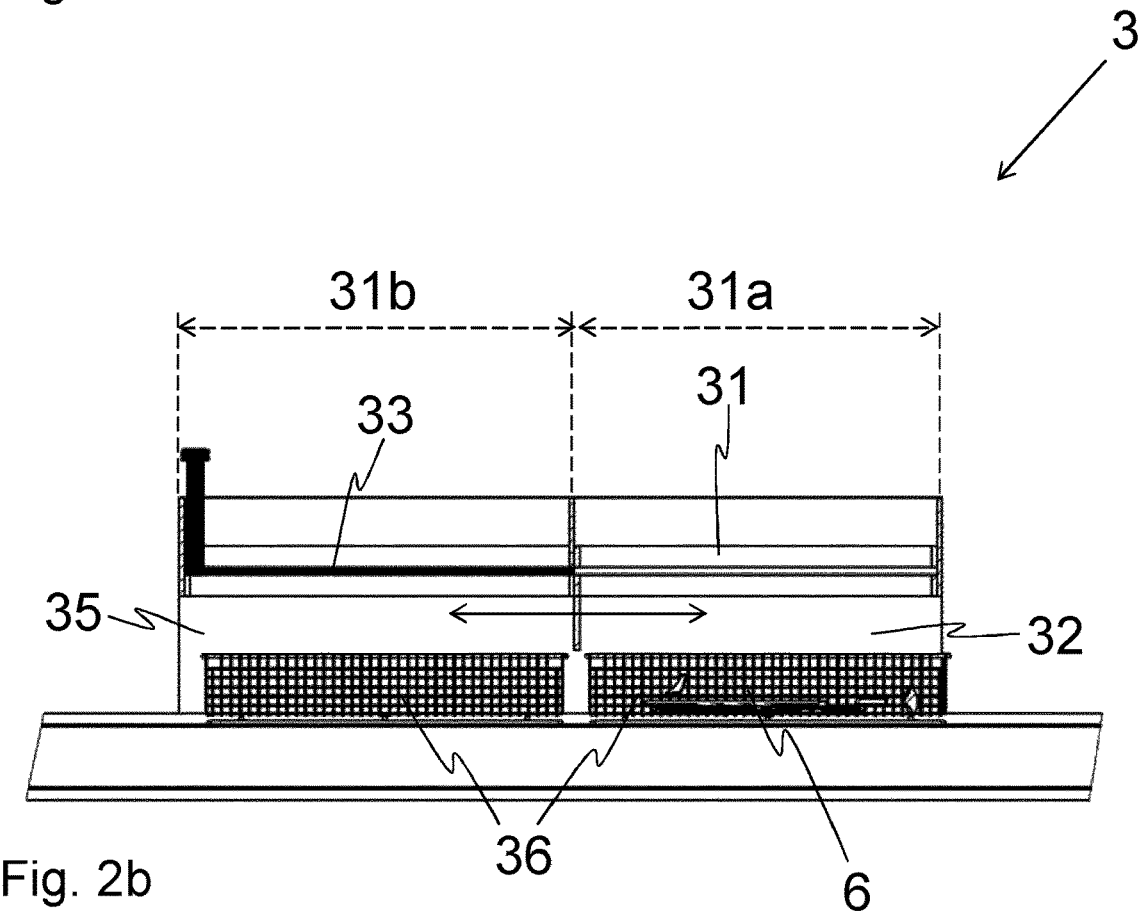
FIG. 2b illustrates the example of the separating apparatus with the presentation surface in a second position.

FIG. 2a and FIG. 2b show detailed views of the separating apparatus 3. The separating apparatus may 3 comprise a frame 31 having a first section 31a and a second section 31b, a compartment 32 arranged at the first section 31a for housing objects 6, and a presentation surface 33 movably arranged in the frame 31. The presentation surface 33 may be located in the first section 31a of the frame 31 in a first position and covers the compartment 32, which is shown in FIG. 2a, and may be located in the second section 31b and provides access to the compartment 32 in a second position, shown in FIG. 2b.

The frame 31 of the separating apparatus 3 may comprise a divider 34 separating the first section 31a from the second section 31b. The divider 34 may be arranged such that the divider 34 prevents objects 6 located on the presentation surface 33 from entering the second section 31b when the presentation surface 33 is moved from the first to the second position.

The separating apparatus 3 may comprise a further compartment 35 for housing objects 6. The second compartment 35 is arranged at the second section 31b. The presentation surface 33 provides access to the further compartment 35 when the presentation surface 33 is in the first position and covers the further compartment 35 when the presentation surface 33 is in the second position.

The compartments 32, 35 may further be configured to allow receptacles 36 for objects 6, such as trays, to be placed inside the compartments. In some embodiments a conveyor belt may transport one or more instrument trays to the separating apparatus 3.

Figure 3:
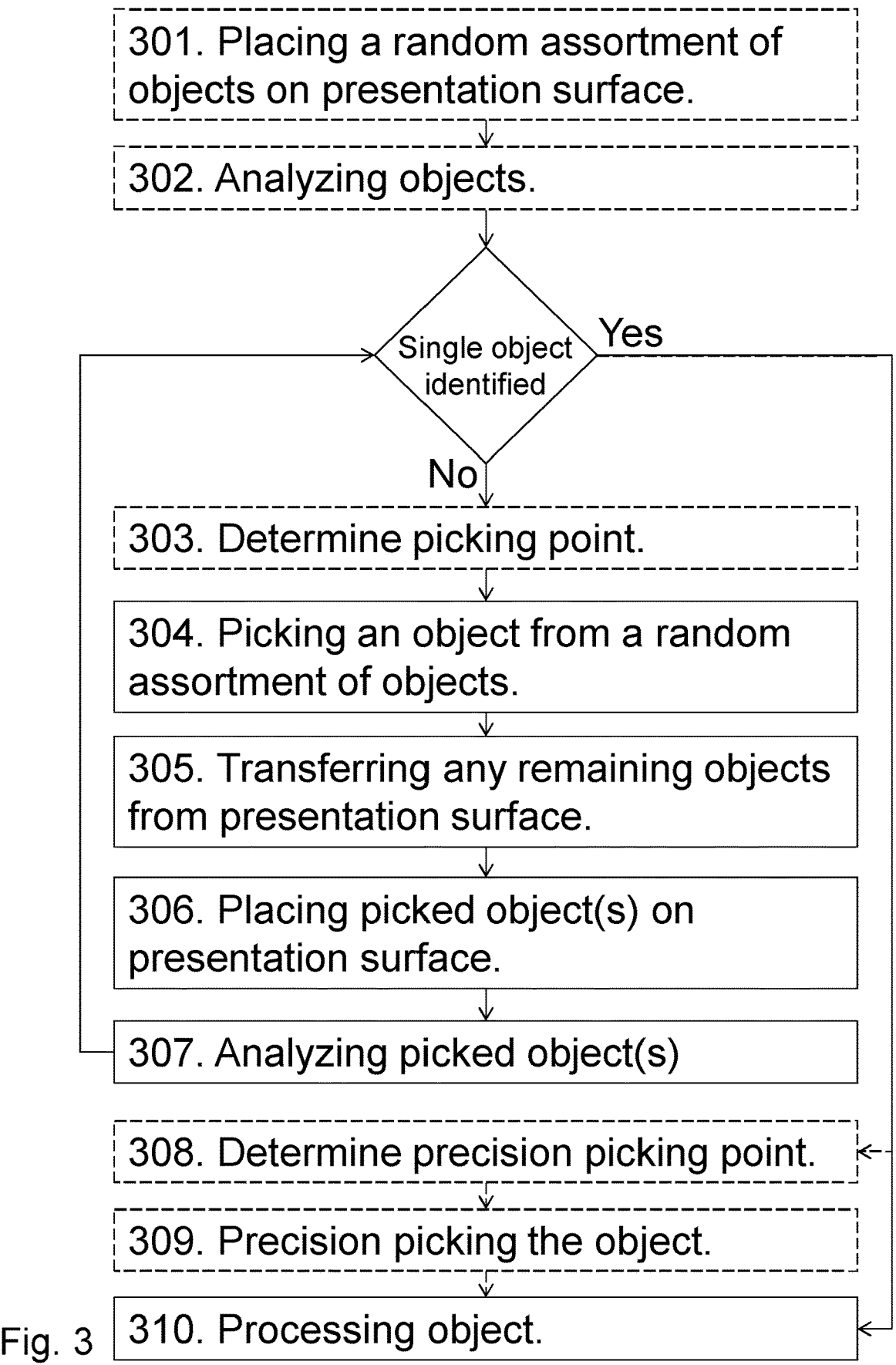
FIG. 3 is a flow diagram illustrating the method for identifying an object according to embodiments herein.

FIG. 3 discloses a method performed by the robotic system 1 for identifying single objects 6 from a random assortment of objects 6. The robotic system 1 comprises the presentation surface 33 arranged to be movable between a first and a second position. In the first position the presentation surface 33 limits access to the compartment 32 and in the second position the presentation surface 33 provides access to the compartment 32. The method comprises one or more of the following actions:

Action 301: The robotic system 1 may place a random assortment of objects on the presentation surface 33.

The objects may e.g. be delivered to the robotic system 1 by means of a conveyor belt. Receptacles 36, such as trays, comprising objects, such as disinfected surgical instruments, from a disinfecting machine, may be loaded onto the conveyor belt and delivered to the separating apparatus 3 by means of the conveyor belt. In some embodiments an empty receptacle 36 may be placed directly in front or behind the filled receptacle 36, e.g. by an automation apparatus or an industrial robot. Both receptacles may be delivered to the separating apparatus 3.

The robotic system 1 may perform a random pick from a tray comprising objects from a disinfecting machine, by means of the picking tool 21, and place the random assortment of objects 6 on the presentation surface 33.

Action 302: The robotic system 1 may analyze the random assortment of objects 6 on the presentation surface 33 in order to identify a single object 6 out of the random assortment. The analyzing may be performed by means of the analyzing apparatus 4 described above with reference to FIG. 1. The analyzing may e.g. be performed by taking a picture of the objects located on the presentation surface 33, by means of an imaging device 41 comprised in the analyzing apparatus 4. The picture may be compared with images stored in an image databank in order to identify the object on the presentation surface 33.

Action 303: When the random assortment of objects 6 has been analyzed and no single object 6 has been identified, the robotic system 1 may determine a picking point 42 for the random assortment of objects 6 arranged on the presentation surface 33. This may e.g. be the case when a plurality of objects 6 are present on the presentation surface 33 which are tangled up in each other in such a way that no clear identification of a single object can be performed.

Action 304: The robotic system 1 picks, among the random assortment of objects 6, an object 6 from the presentation surface 33. When a picking point 42 has been determined, the robotic system 1 may pick the object 6 from the presentation surface 33 at the determined picking point 42.

Action 305: When the object has been picked from the presentation surface 33, any remaining objects 6 on the presentation surface 33 are removed from the presentation surface 33. The remaining objects may e.g. be removed from the presentation surface 33 by being transferred to a compartment arranged below the presentation surface 33. The objects may be transferred to the compartment 32 by moving the presentation surface 33 from the first position to the second position, such that access is provided to the compartment 32 below the presentation surface 33. The presentation surface 33 may e.g. be slid from the first position to the second position or may be tilted from the first position to the second position. Due to the movement of the presentation surface 33, any objects 6 remaining on the presentation surface 33 will fall into the compartment 32 below the presentation surface 33 or into a receptacle 36 located in the compartment 32.

The frame may comprise a divider 34 separating the first section 31a and the second section 31b of the frame 31. Due to the divider 34, the objects 6 located on the presentation surface 33 will be prevented from entering the second section 31b when the presentation surface 33 slides from the first section 31a to the second section 31b. The divider 34 may e.g. be shaped as a rake which scrapes the objects 6 off the presentation surface 33 and into the compartment 32. When the remaining objects 6 have been removed from the presentation surface 33, the presentation surface 33 may be moved back to the first position.

The presentation surface 33 may in some embodiments be moved by means of a second robot arm 5. However, other driving means suitable for moving the presentation surface 33 from the first position to the second position, such as a belt, a chain or a rope drive, a pinion rack or the like, may also be used to perform the movement of the presentation surface 33 between the first and the second position.

Action 306: When the remaining objects 6 have been removed from the presentation surface 33, the robotic system 1 places the gripped object(s) 6 onto the presentation surface 33. This may also be referred to as the picked object(s) 6 being returned to the presentation surface 33. The robotic system 1 may prior to placing the gripped object(s) on the presentation surface 33 move the presentation surface 33 back to the first position where it covers the compartment 32.

Action 307: When the picked object(s), which is a reduced selection, have been placed on the presentation surface 33, the robotic system 1 performs an analysis of the picked object(s) 6 on the presentation surface 33 in order to identify a single object 6. If an analysis has already been performed as disclosed in action 302 this analysis may also be referred to as second analysis. If one single object 6 was picked in action 304 the object 6 may be identified.

However, in some cases objects 6 may be tangled up in each other, such that a plurality of objects 6 is picked from the presentation surface 33 in action 304. If the robotic system 1 is not able to identify a single object 6 from the selection on the presentation surface 33, the robotic system 1 may return to action 303 in order to further reduce the number of objects 6 on the presentation surface 33. Thereby, the probability of a successful identification of a single object 6 can be increased.

Action 308: When a single object 6 has been successfully identified, the robotic system 1 may determine a precision picking point. The precision picking point may be a point suitable for gripping the object 6 in order to be able to process the object 6 further. One example of a precision picking point may e.g. be at a pivot point of a pair of scissors and/or pliers. By gripping the scissors or pliers at the pivot point the scissors or pliers may be closed in preparation for the next use. The precision picking point may however also be selected in order to facilitate inspection of the object 6.

Action 309: When a precision picking point has been determined, the robotic system 1 may perform a precision picking of the object 6 at the determined precision picking point using the picking tool 21. The precision picking point is a point on the object 6 selected in order to facilitate performing a processing step on the object 6, whilst the picking point 42, as discussed in Action 303 above, is a point selected for making a pick from the random assortment of objects 6 in order to reduce the number of objects 6 on the presentation surface 33.

Action 310: When a single object 6 has been identified, the robotic system 1 may process the single object 6. The processing may e.g. comprise one or more of the steps of taking an inventory of the provided objects 6, checking cleanliness of the object 6, such as checking for tissue residue on an instrument, checking for damage and wear of the object 6, assessing sharpness of bladed instruments, lubricating moving parts, closing and locking of jointed instruments.

The processing may further comprise placing the object 6 at a second location for processed objects 6, which is separated from the first compartment 32 comprising unprocessed objects 6. The second location may e.g. be the second compartment 35 of the separating apparatus 3, a second receptacle 36, such as a tray, in the separating apparatus 3 and/or a receptacle 36, such as a tray, located in the second compartment 35 of the separating apparatus 3. The objects 6 may e.g. be sorted according to type of object during the placement of the objects 6 at the second location. The processing 310 may also comprise repacking of the object 6, for example by wrapping the object 6 and/or a plurality of identified objects in protective paper and autoclaving of the object(s) 6.

Figure 4:
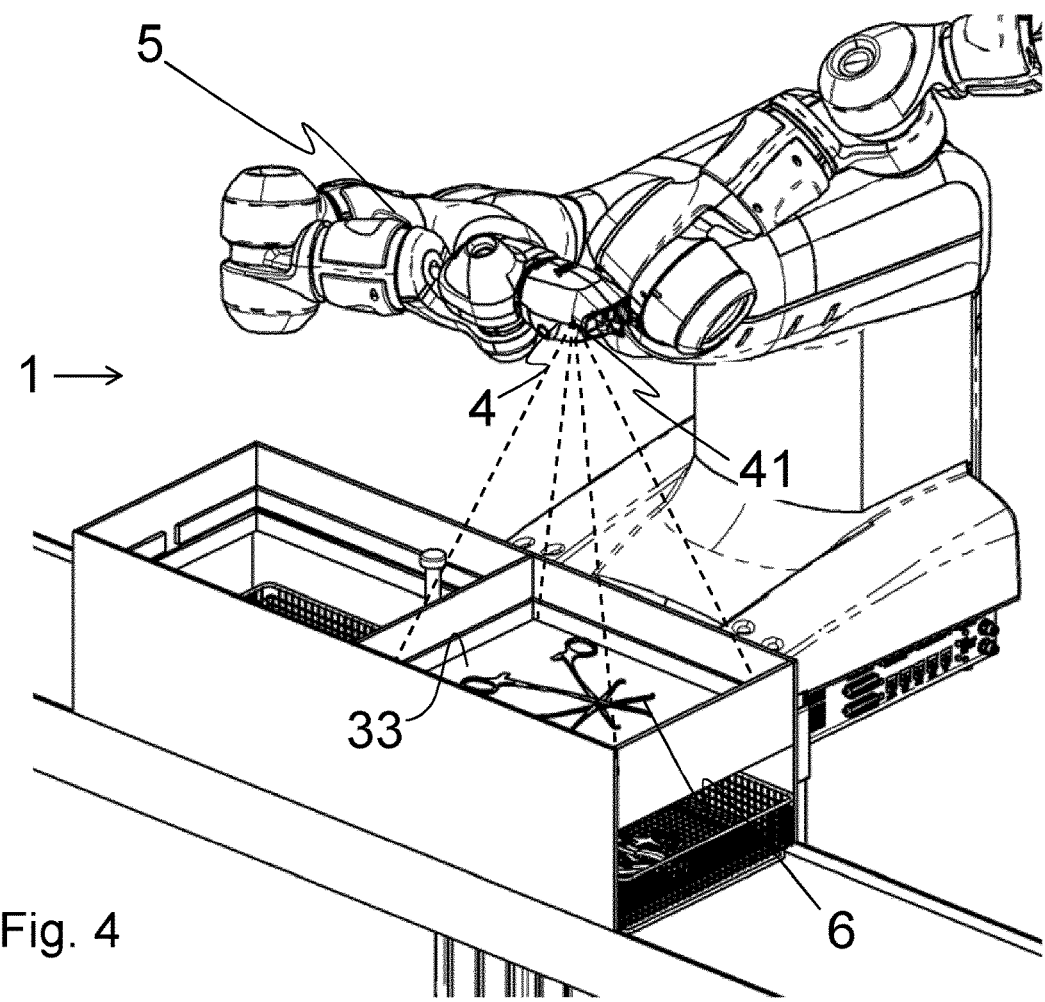
FIG. 4 illustrates an exemplifying step of analyzing a random assortment of objects.

FIG. 4 discloses the step of analyzing according to one embodiment herein. The analyzing may e.g. be performed by taking a picture of the objects located on the presentation surface 33, by means of the imaging device 41 comprised in the analyzing apparatus 4. The picture may be compared with images stored in an image databank in order to identify the object on the presentation surface 33. According to the embodiment shown in FIG. 4 the analyzing apparatus 4 may be comprised in the second robot arm 5. This step corresponds to Action 302 described above in relation to FIG. 3.

When only a single object is located on the surface 33, the object may be identified and the object may be picked up and passed onto the processing step 310 of the method.

Figure 5:
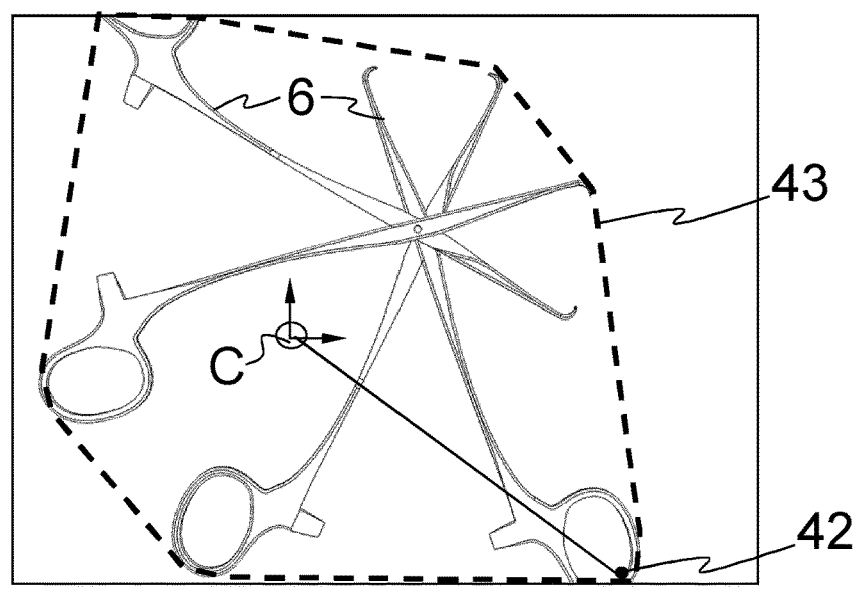
FIG. 5 illustrates an exemplifying step of determining a picking point for the random assortment of objects.

FIG. 5 shows the step of determining of the picking point 42. The picking point 42 may be defined as the point furthest away from a centroid C, i.e. a geometric center, of the bounding box 43 of the objects 6 visible in the image. The robotic system 1 may e.g. apply a bounding box 43 to the picture of the assortment of objects 6 by drawing lines between the outmost points of the objects 6, such that all points of the objects 6 fall within the area of the drawn lines. Applying the bounding box 43 to the picture may e.g. be performed by the imaging device 41. This step corresponds to Action 302 described above in relation to FIG. 3.

Figure 6:
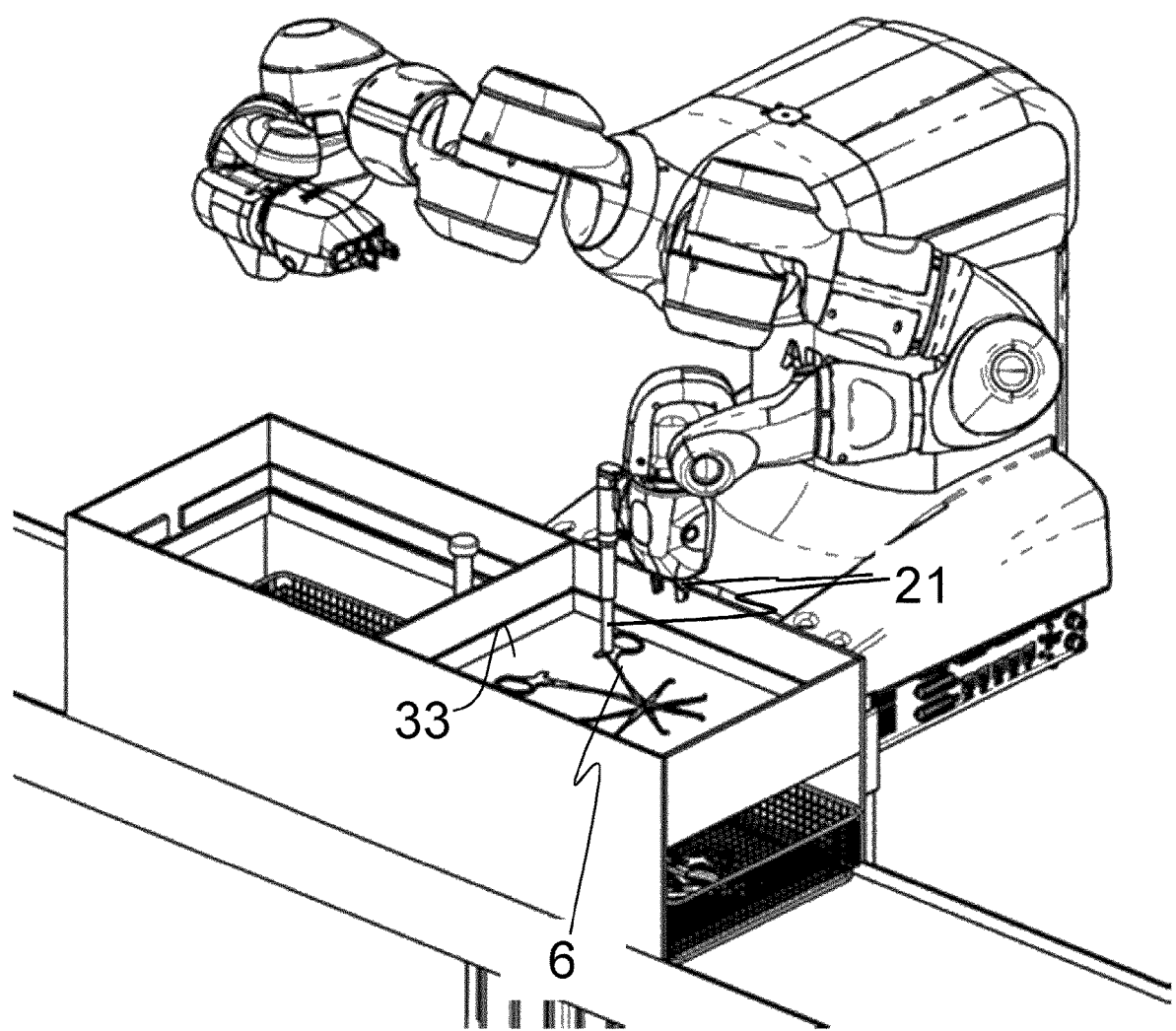
FIG. 6 illustrates an exemplifying step of picking an object at the determined picking point.
Figure 7:
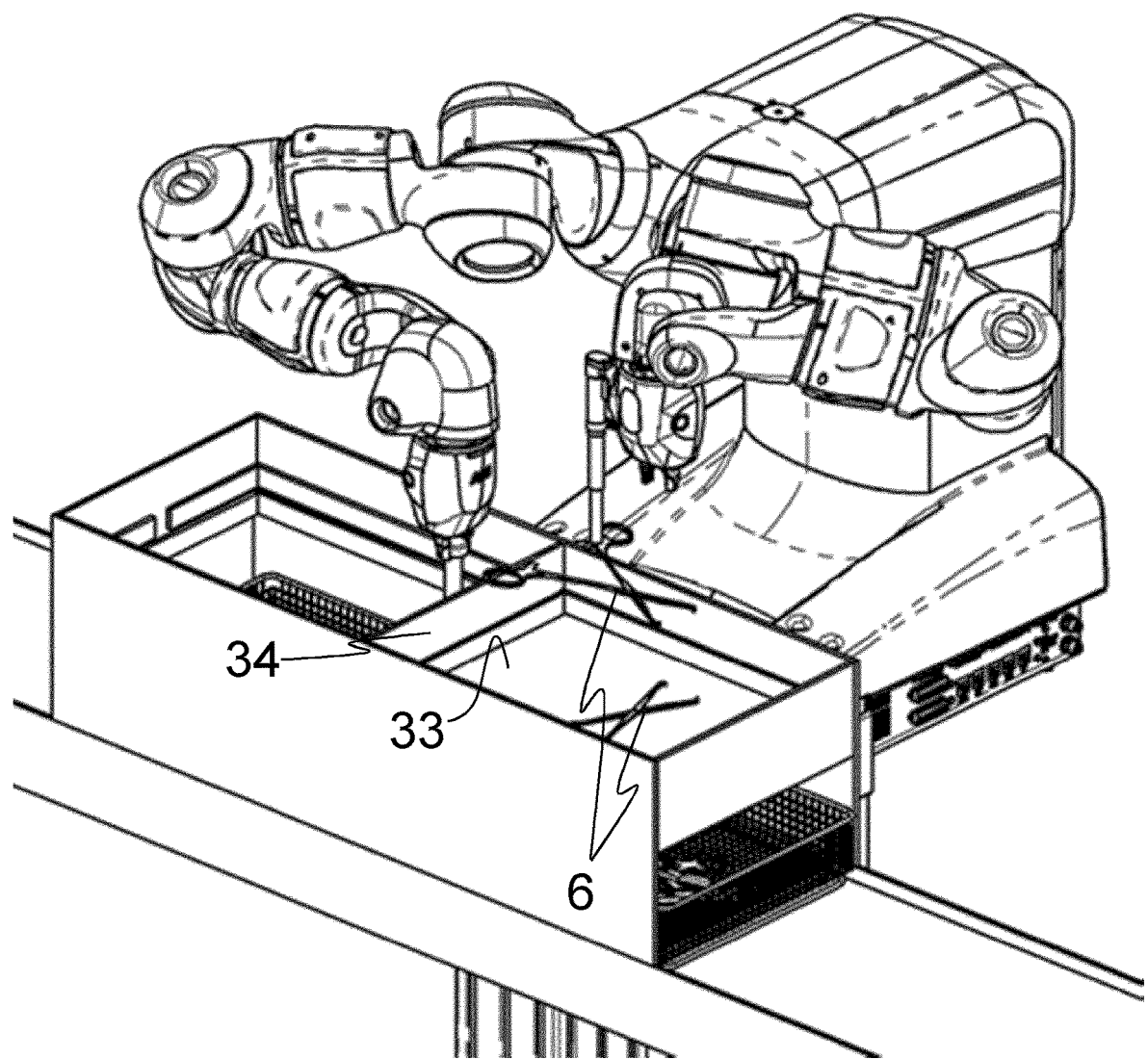
FIG. 7 illustrates the random assortment of objects arranged on the presentation surface prior to reducing the selection.

FIG. 6 shows the step of picking, among the random assortment of objects 6, an object 6 from the presentation surface 33 at the determined picking point 42. This step corresponds to Action 304 described in relation to FIG. 3. The picking may e.g. be performed by means of the picking tool 21. Picking may herein also be referred to as gripping or grabbing FIG. 7 shows the step of the robotic system 1 lifting the object 6 clear from the presentation surface 33 in preparation for moving the presentation surface 33 from the first position to the second position as described in Action 305 above.

Figure 8:
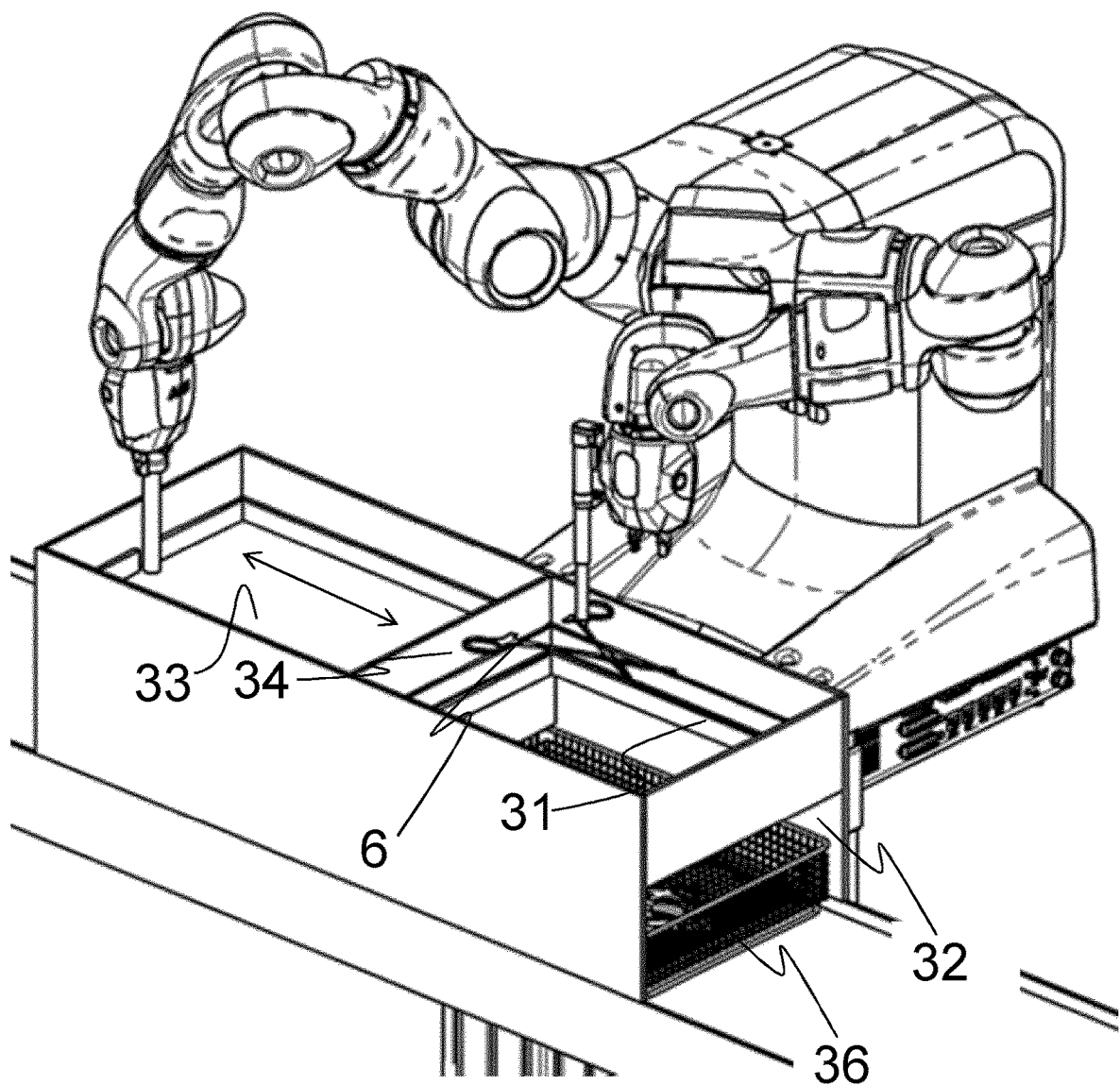
FIG. 8 illustrates an exemplifying step of moving the presentation surface from a first position to a second position to reduce the selection of objects.

FIG. 8 shows the step of moving the presentation surface 33 from the first position to the second position, such that access is provided to the compartment 32 below the presentation surface 33. Thereby, the one or more objects 6 remaining on the presentation surface 33 will fall into the compartment 32 below the presentation surface. This step corresponds to Action 305 described above in relation to FIG. 3.

Figure 9:
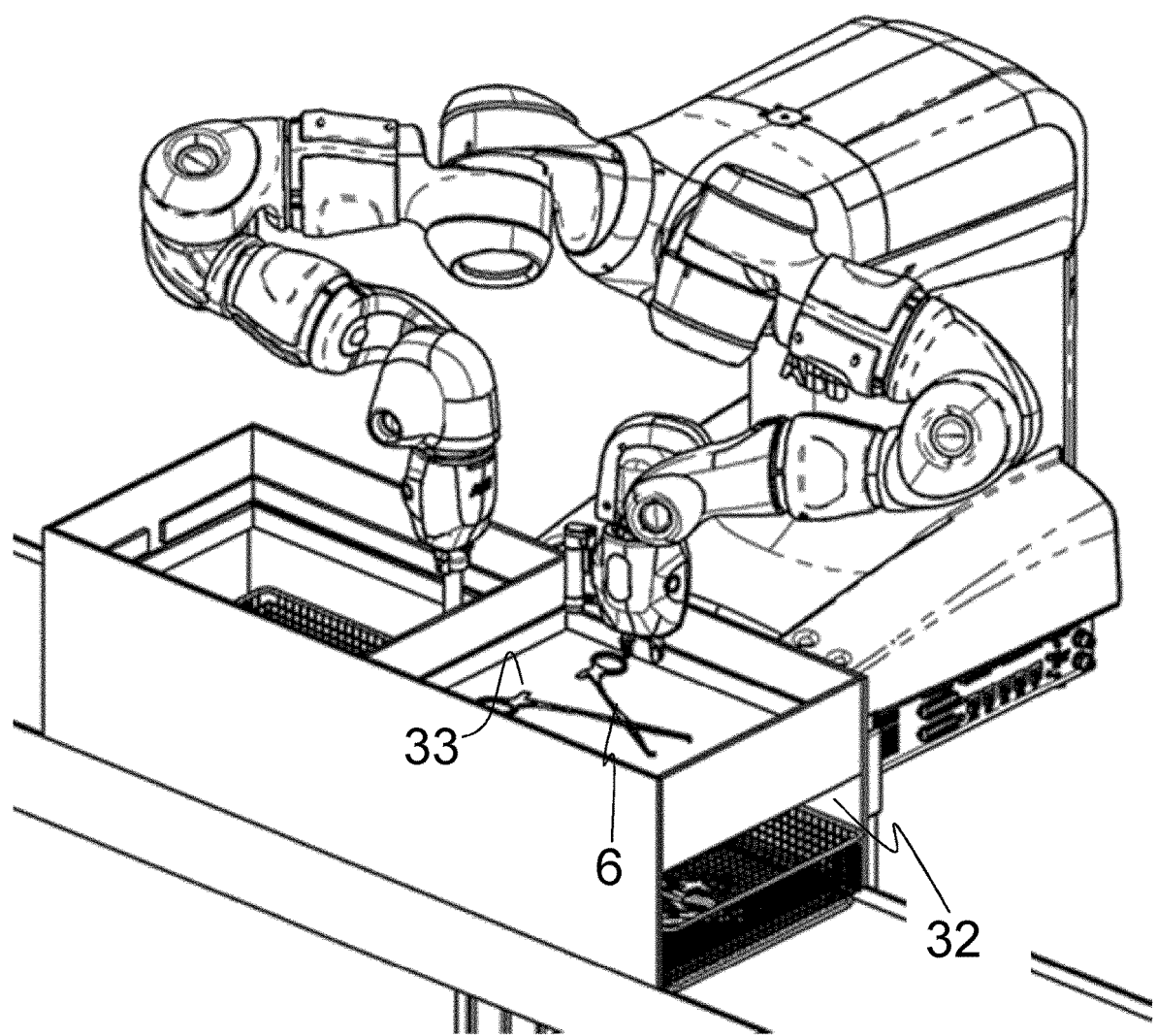
FIG. 9 illustrates an exemplifying step of placing the picked object on the presentation surface after the selection has been reduced.

FIG. 9 shows the step of the robotic system 1 placing the gripped object(s) 6 onto the presentation surface 33. The robotic system 1 may prior to placing the gripped objects 6 on the presentation surface 33 move the presentation surface 33 back to the first position where it covers the compartment 32. This step corresponds to Action 306 described above in relation to FIG. 3. When the picked object(s) 6, which is a reduced selection, have been placed on the presentation surface 33, the robotic system 1 performs another analysis of the picked object(s) 6 on the presentation surface 33 in order to identify a single object 6. If only one single object 6 was picked in action 304 the object 6 is identified.

Figure 10:
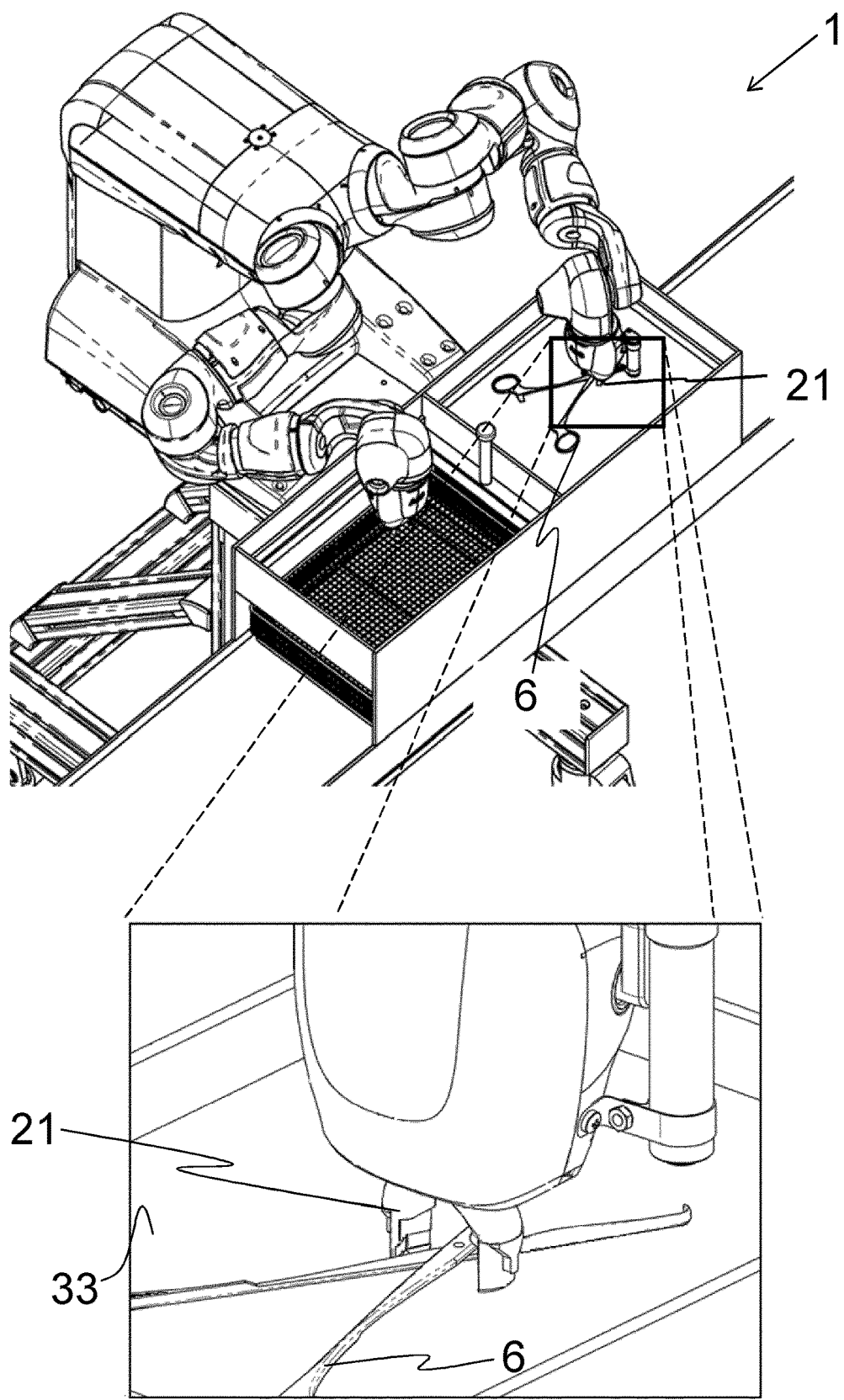
FIG. 10 illustrates an exemplifying step of precision picking an identified object from the presentation surface.

FIG. 10 shows the step of precision picking an object according to an embodiment herein, in which the object 6 is a pair of surgical forceps and the precision picking point is at a pivot point of the forceps. This step corresponds to Action 309 described above in relation to FIG. 3. By picking the forceps at the pivot point the forceps may be closed before further processing of the forceps.

It will be appreciated that the foregoing description and the accompanying drawings represent non-limiting examples of the methods and apparatus taught herein. As such, the inventive apparatus and techniques taught herein are not limited by the foregoing description and accompanying drawings. Instead, the embodiments herein are limited only by the following claims and their legal equivalents.

The invention claimed is:

1. A method performed by a robotic system, for identifying single objects from a random assortment of objects, wherein the method includes:
   picking, among a random assortment of objects on a presentation surface, an object from the presentation surface at a determined picking point,
   removing any remaining objects from the presentation surface,
   placing the picked object on the presentation surface after the removal of said any remaining objects from the presentation surface,
   analyzing the picked object on the presentation surface, in order to identify a single object.

2. The method according to claim 1, wherein the method further includes:
   placing a random assortment of objects on the presentation surface.

3. The method according to claim 1, wherein the method further includes:
   analyzing a random assortment of objects on the presentation surface in order to identify a single object out of the random assortment.

4. The method according to claim 1, wherein the method further includes:
   determining a precision picking point, when successfully identifying the single object.

5. The method according to claim 4, wherein the method further includes:
   precision picking the object at the determined precision picking point.

6. The method according to claim 1, wherein the analyzing includes comparing an image of the objects on the presentation surface with stored images of the objects.

7. The method according to claim 1, wherein the removing includes transferring the remaining objects from the presentation surface to a compartment arranged below the presentation surface, by moving the presentation surface from a first position to a second position.

8. The method according to claim 1, wherein the method further includes:
determining a picking point for the random assortment of objects arranged on the presentation surface, when the random assortment of objects has been analyzed and no single object is identified.

9. The method according to claim 8, wherein the picking point is located furthest away from a centroid of a bounding box of the objects on the presentation surface.

10. The method according to claim 1, wherein the method further includes:
processing the single object, when a single object is identified.

11. The method according to claim 10, wherein the processing includes inspecting, lubricating and/or sharpness testing of the object.

12. The method according to claim 10, wherein the processing further includes positioning the object in a further compartment.

13. A robotic system for identifying single objects from a random assortment of objects, the robotic system comprising:
a first robot arm including a picking tool for picking objects,
a separating apparatus including a frame having a first section and a second section, a compartment arranged at the first section for housing objects, and a presentation surface movably arranged in the frame, wherein the presentation surface in a first position is located in the first section of the frame and covers the compartment, and in a second position is located in the second section and provides access to the compartment,
an analyzing apparatus for identifying objects, which objects are located on the presentation surface, and
a second robot arm for moving the presentation surface between the first and the second sections.

14. The robotic system according to claim 13, wherein the frame of the separating apparatus includes a divider separating the first section from the second section, arranged such that the divider prevents objects located on the presentation surface from entering the second section when the presentation surface moves from the first section to the second section.

15. The robotic system according to claim 13, wherein the analyzing apparatus includes an imaging device for generating an image of objects located on the presentation surface.

16. The method according to claim 2, wherein the method further includes:
analyzing a random assortment of objects on the presentation surface in order to identify a single object out of the random assortment.

17. The method according to claim 2, wherein the method further includes:
determining a precision picking point, when successfully identifying the single object.

18. The method according to claim 2, wherein the analyzing includes comparing an image of the objects on the presentation surface with stored images of the objects.

19. The method according to claim 2, wherein the removing includes transferring the remaining objects from the presentation surface to a compartment arranged below the presentation surface, by moving the presentation surface from a first position to a second position.

* * * * *